United States Patent [19]

Favre-Bulle et al.

[11] Patent Number: 5,814,497
[45] Date of Patent: Sep. 29, 1998

[54] ENZYMATIC HYDROLYSIS OF RACEMIC A-SUBSTITUTED 4-METHYLTHIOBUTYRONITRILES USING A NITRILASE FROM ALCALIGENES FAECALIS, GORDONA TERRAE OR RHODOCOCCUS SP

[75] Inventors: Olivier Favre-Bulle, Lyon; Maria-Claude Bontoux, Luzinay; Denis Largeau, Vourles; André Ariagno, Francheville, all of France

[73] Assignee: Rhone-Poulenc Nutrition Animale, Antony, France

[21] Appl. No.: 809,184

[22] PCT Filed: Sep. 19, 1995

[86] PCT No.: PCT/FR95/01196

§ 371 Date: Mar. 20, 1997

§ 102(e) Date: Mar. 20, 1997

[87] PCT Pub. No.: WO96/09403

PCT Pub. Date: Mar. 28, 1996

[30] Foreign Application Priority Data

Sep. 22, 1994 [FR] France .................................. 94 11301
Mar. 7, 1995 [FR] France .................................. 95 02615

[51] Int. Cl.$^6$ ..................................................... C12P 11/00
[52] U.S. Cl. ........................... 435/130; 822/829; 822/146
[58] Field of Search ...................................... 435/130, 146, 435/829

[56] References Cited

FOREIGN PATENT DOCUMENTS

| 0 348 901 A2 | 1/1990 | European Pat. Off. . |
| 0 444 640 A2 | 9/1991 | European Pat. Off. . |
| 0 610 048 A2 | 8/1994 | European Pat. Off. . |
| 0 610 049 A2 | 8/1994 | European Pat. Off. . |
| 4-40899 | 2/1992 | Japan . |

OTHER PUBLICATIONS

Bhalla et al., "Asymmetric hydrolysis of alpha aminonitriles to optically active amino acids by a nitrilase of *Rhodococcus rhodochrous* PS–34", Appl. Microbiol. Biotechnol. 37(2):184–90 (1992).
ATCC Bacteria and Bacteriophages, p. 157 (1992).
Chemical Abstract, vol. 117:46744h, Aug. 3, 1992.
Chemical Abstract, vol. 116:254079x, Jun. 22, 1992.

*Primary Examiner*—Sandra E. Saucier
*Attorney, Agent, or Firm*—Finnegan, Henderson, Farabow, Garrett & Dunner, L.L.P.

[57] ABSTRACT

A method for the enzymatic hydrolysis of racemic α-substituted 4-methylthiobutyronitriles into racemic α-substituted 4-methylthiobutyric acid using a nitrilase from *Alcaligenes faecalis, Gordona terrae* or *Rhodococcus sp.*

15 Claims, No Drawings

ENZYMATIC HYDROLYSIS OF RACEMIC A-SUBSTITUTED 4-METHYLTHIOBUTYRONITRILES USING A NITRILASE FROM ALCALIGENES FAECALIS, GORDONA TERRAE OR RHODOCOCCUS SP

The present invention relates to the use of a nitrilase as a catalyst for hydrolysing a nitrile group into a carboxylic group. The invention relates more precisely to the use of the nitrilase chosen from nitrilases of microorganisms of the genus Alcaligenes, Rhodococcus or Gordona and more precisely of *Alcaligenes faecalis* deposited under the number ATCC 8750, *Rhodococcus sp.* HT 29-7 deposited under the number FERM BP-3857 or *Gordona terrae* MA-1 deposited under the number FERM BP-4535.

The nitrilase of *Alcaligenes faecalis* is described, for example, in the European and Japanese patents published under the numbers EP 348,901 and JP 03 224 496 respectively, both belonging to the Asahi company. In these patents, and more particularly in the European patent, the nitrilase is used to produce optically active acids from racemic nitriles. The preferred starting nitriles are α-substituted and contain an alkyl chain preferably containing 1 to 3 carbon atoms or an aromatic radical. Example 11 of the abovementioned European patent describes the hydrolysis of racemic mandelonitrile with *Alcaligenes faecalis*; the R-(-)-mandelic acid is obtained in an enantiomeric excess of 91%. European patent 486,289 and its equivalent American patent U.S. Pat. No. 5,326,702 from the company Nitto Chemical describe the use of *Alcaligenes sp.* BC35-2 (FERM No. 11265 or FERM-BP-3318) to hydrolyse mandelonitrile in the presence of a sulphite; in this case, mandelic acid is obtained in an enantiomeric excess of about 98%.

Patent JP 04 341 185 from the company Asahi also describes the preparation and use of the nitrilase from *Alcaligenes faecalis* ATCC 8750 to solve the problems of preparation of optically pure compounds from their racemic nitrile. The enantioselective nitrilase described in the Japanese patent referred to above is more preferably capable of hydrolysing the 2-hydroxynitrile of general formula (I) below into 2-hydroxycarboxylic acid of formula (II) below:

in which R represents an optionally substituted aryl group or an optionally substituted heterocyclic group. It is mentioned in that patent that hydrolysis of the nitrile of mandelic acid by the said nitrilase makes it possible to obtain a 100% enantiomeric excess of R-(-)-mandelic acid. It is mentioned in Example 5 that the said nitrilase may be used to hydrolyse aliphatic nitrites such as valeronitrile, acrylonitrile, 2-halopropionitriles and chloroacetonitrile. Nothing is specified as regards the enantioselectivity of this hydrolysis on aliphatic nitriles having an asymmetric centre.

The said text also specifies that the nitrilase of *Alcaligenes faecalis* is of optimum activity at a pH between 6.5 and 8.0; the working temperature of the said enzyme should, according to that reference, always be below 45° C.

It appeared to be entirely surprising that the said enzyme of *Alcaligenes faecalis* ATCC 8750, when used to hydrolyse 4-methylthio-2-hydroxybutyronitrile, carried out this hydrolysis without any selectivity from the point of view of the optical purity. This enzyme hydrolyses the said nitrile producing a racemic mixture of the two acids with no preponderance of either of the isomers.

The nitrilase of *Rhodococcus sp.* HT 29-7 deposited under the number FERM BP-3857 is described, for example, in the European and American patents published under the numbers EP 610,049 and U.S. Pat. No. 5,296,373 respectively, both belonging to the company Nitto.

In these patents, and particularly in the American patent, the nitrilase is used to produce optically active acids from racemic nitriles bearing a phenyl group. The starting nitriles all contain an aromatic radical; this essentially involves hydrolysis of mandelonitrile or of derivatives thereof substituted on the aromatic ring. Example 1 of the abovementioned American patent describes the hydrolysis of racemic mandelonitrile with *Rhodococcus sp.* HT 29-7; the R-(-)-mandelic acid is obtained in an enantiomeric excess of 100%. Example 2 describes the hydrolysis of substituted mandelonitrile derivatives on the ring; the enantiomeric excess of mandelic acid derivative is also 100% and this is likewise the case when the hydrolysis is carried out on benzaldehyde nitrites.

European patent 610 049 from the company Nitto Chemical describes the use of *Rhodococcus sp.* HT 29-7 (FERM BP-3857), of *Alcaligenes sp.* BC35-2 (FERM BP-3318) or of *Brevibacterium acetylicum* IAM 1790 to hydrolyse α-hydroxynitriles substituted in the γ position with an aromatic ring into α-hydroxycarboxylic acid substituted with an optically active phenyl group. The acids obtained with *Rhodococcus sp.* HT 29-7 always have a variable enantiomeric excess depending on the starting nitrile and on the presence or absence of phosphoric acid (pH set at about 8.2).

It appeared to be entirely surprising that the said enzyme of *Rhodococcus sp.* HT 29-7 (FERM BP-3318), when used to hydrolyse 4-methylthio-2-hydroxybutyronitrile, carried out this hydrolysis without any enantiomeric selectivity. This enzyme hydrolyses the said nitrile producing a racemic mixture of the two acids without any preponderance of either of the isomers.

The nitrilase of *Gordona terrae* MA-1 deposited under the number FERM BP-4535 is described in European patent 0,610,048 to hydrolyse nitrites bearing a γ-phenyl group and an α-hydroxy group into the corresponding optically active acid. The enantiomeric excess ranges in all the examples between 92 and 100%.

It appeared to be entirely surprising that the said enzyme of *Gordona terrae* MA-1 filed under the number FERM BP-4535, when used to hydrolyse 4-methylthio-2-hydroxybutyronitrile, carried out this hydrolysis without any enantiomeric selectivity. This enzyme hydrolyses the said nitrile producing a racemic mixture of the two acids without any preponderance of either of the isomers.

The present invention thus relates to a process for the preparation of racemic α-substituted 4-methylthiobutyric acids by hydrolysis of racemic α-substituted 4-methylthiobutyronitriles with the nitrilase of one of the following microorganisms: *Alcaligenes faecalis* filed under the number ATCC 8750, *Rhodococcus sp.* HT 29-7 filed under the number FERM BP-3857 or *Gordona terrae* MA-1 filed under the number FERM BP-4535.

According to the process of the invention, the microorganism may be used as it is or immobilized on supports which are well known to those skilled in the art.

Moreover, the genetic information which codes for the enzyme may be transferred from the parent microorganism (such as *A. faecalis* ATCC8750, etc.) into a microorganism such as *Bacillus subtilis*.

One variant of the process of the invention consists in using, in place of a microorganism, a corresponding amount of its free or immobilized enzyme, this enzyme being totally or partially purified.

Among the α-substituted 4-methylthiobutyronitriles, it is preferred to use 4-methylthio-2-hydroxybutyronitrile, which makes it possible to prepare the hydroxy analogue of racemic methionine. This technique for the preparation of methionine derivatives makes it possible to avoid the formation of large amounts of inorganic side products whose disposal causes ever-increasing problems on account of environmental protection constraints.

In the context of the present invention, these enzymes have a nitrilase activity in a pH range between 4 and 11 and optimum activity at a pH of between 5 and 9. Their optimum working temperature is between 30° and 60° C.; it is preferred, however, to use them between 30° and 50° C.

It is preferred to work with a nitrile concentration in the starting solution of between 10 mmol and 400 mmol per liter and preferably between 50 and 200 mmol per liter. The concentration of ammonium salt of the acid obtained has little influence on the activity of the enzyme when it is less than 2 mol per liter and it is preferably between 0.1 and 1.5 mol per liter.

The invention will be described more fully with the aid of the examples which follow, which should not be considered as limiting the invention.

EXAMPLE 1

The microorganism *Alcaligenes faecalis* ATCC 8750 is cultured in the following medium:

ammonium acetate 10 g/l yeast extract 5 g/l peptone 5 g/l $K_2HPO_4$ 5 g/l $MgSO_4.7H_2O$ 0.2 g/l $FeSO_4.7H_2O$ 30 mg/l NaCl 1 g/l benzonitrile 0.5 g/l pH 7.2

Culturing is carried out at 30° C. in 2 liter conical flasks containing 600 ml of medium. The whole mixture is stirred at 150 revolutions per minute for 30 hours. The cell pellet is recovered, washed with 9 g/l NaCl solution and then frozen.

Operating conditions to hydrolyse the butyronitrile:

4-methylthio-2-hydroxybutyronitrile 50 mM cells 5 mg/ml phosphate buffer 200 mM temperature 30° C.

duration 4 hours

Study of the kinetics of hydrolysis of 4-methylthio-2-hydroxybutyronitrile shows a linear production of 2.8 μmol of hydroxy analogue of methionine per hour and per mg of dry cells. The enantiomeric excess of the acid formed was measured by liquid chromatography; it is equal to 0% for a yield of acid of 80%.

EXAMPLE 2

The stability of the enzyme was evaluated according to the kinetics of production of the hydroxy analogue of methionine over 180 hours with free cells.

The operating conditions are as follows:

4-methylthio-2-hydroxybutyronitrile 100 mM cells 10 mg/ml phosphate buffer 300 mM 5 ml temperature 25° C.

The nitrile is added sequentially by addition of 100 mmol of nitrile after depletion. The formation of the corresponding acid is indicated in Table I

| TIME | Acid formed (mmol/liter) | Activity (μmol/h · mg of cell · s) |
|---|---|---|
| 0 | 0 | 0 |
| 2 h | 39 | 1.7 |
| 17 h | 230 | 1.3 |
| 24 h | 312 | 1.7 |
| 47 h | 466 | 1.2 |
| 70 h | 556 | 0.4 |
| 172 h | 860 | 0.6 |
| 180 h | 940 | 0.6 |

The initial activity is 2 μmol/h.mg of dry cells. This example proves the stability of the enzyme despite the presence of high concentrations of acid (0.9 mol of hydroxy analogue of methionine).

EXAMPLE 3

The stability of the enzyme as a function of the amount of substrate and of the amount of acid formed was also measured under the following conditions:

Stability of the enzyme as a function of the amount of substrate nitrile cf table of results cells 10 mg/ml phosphate buffer 300 mM pH 7.0 5 ml temperature 25° C.

duration 1 hour

| Nitrile concentration (mM) | Activity (μmol/h · mg of cell · s) |
|---|---|
| 50 | 2 |
| 100 | 2 |
| 150 | 2 |
| 200 | 2 |
| 500 | 0 |

Stability of the enzyme as a function of the amount of acid formed operating conditions:

nitrile 50 mM cells 2.5 mg/ml phosphate buffer 100 mM pH 7.0 1 ml temperature 30° C.

duration 2 hours

| Acid concentration (mM) | Activity (μmol/h · mg of cell · s) |
|---|---|
| 0 | 3.2 |
| 100 | 4.5 |
| 200 | 3.8 |
| 300 | 4.1 |
| 400 | 4 |

-continued

| Acid concentration (mM) | Activity (μmol/h · mg of cell · s) |
|---|---|
| 500 | 4 |
| 600 | 3.4 |
| 700 | 2.8 |

EXAMPLE 4

Purification of the Nitrilase The cells of *Alcaligenes faecalis* are cultured for 24 hours at 30° C. in the medium described in Example 1.

After centrifuging the culture, the pellet is taken up in pH 7.5 buffer (25 mM trisHCl, 10% (w/v) glycerol). The cell suspension-is treated with ultrasound and then centrifuged in order to obtain the crude extract. The crude extract is then treated with ammonium sulphate up to 30% of saturation. The precipitate obtained is resuspended in pH 7.5 buffer and then dialysed against 2 liters of the same buffer overnight.

The solution obtained is then loaded onto a Q Sepharose Fast Flow ER 26/10™ anion-exchange column pre-equilibrated with the pH 7.5 buffer. The activity is then eluted with a gradient of 0 to 1M NaCl.

The active fractions are then loaded onto a Mono Q HR 5/5™ anion-exchange column pre-equilibrated with pH 7.5 buffer. The nitrilase is eluted using a gradient of 0 to 1M NaCl.

Lastly, the fractions containing the activity are combined and 1M ammonium sulphate is then added. This solution is loaded onto a Phenyl Sepharose HR 5/5™ hydrophobic-interaction column pre-equilibrated with the pH 7.5 buffer, to which is added 1M $(NH_4)_2SO_4$. The activity is then eluted with a gradient of 1 to 0M ammonium sulphate.

The molecular weight of the protein is determined by gel filtration. It is about 260 kDa. A single band of 43 kDa is observed on SDS-PAGE (purity of 95%).

The kinetics of hydrolysis of the 4-methylthio-2-hydroxybutyronitrile into the hydroxy analogue of methionine with the nitrilase of *A. faecalis* is linear.

| Time (hour) | Activity (μmol/h · mg of prot.) | RY (%) |
|---|---|---|
| 0 | 0 | 1 |
| 0.5 | 150 | 3 |
| 1 | 171 | 5 |
| 21.5 | 150 | 68 |
| 24.8 | 150 | 77 |
| 29 | 150 | 87 |

EXAMPLE 5

Influence of the pH

Operating conditions:

nitrile 50 mM protein 50 μg/ml acetate buffer 100 mM of pH 4 to 5 phosphate buffer 100 mM of pH 6 to 7 1 ml

Tris-HCl buffer 100 mM of pH 8 to 9 borate buffer 100 mM of pH 10 to 11 temperature 30° C.

duration 1 to 2 hours

| pH | Activity (μmol/h · mg of prot.) |
|---|---|
| 4 | 0 |
| 5 | 42 |
| 6 | 232 |
| 7 | 272 |
| 8 | 405 |
| 9 | 412 |
| 10 | 158 |
| 11 | 0 |

EXAMPLE 6

Influence of the Temperature

Operating conditions:

nitrile 50 mm protein 50 μg/ml phosphate buffer 100 mM of pH 7.0 variable temperatures from 4° C. to 60° C.

duration 1 hour

The optimum working temperature of the enzyme is 50° C.

| Temperature in °C. | Activity (μmol/h · mg of prot.) |
|---|---|
| 4 | 45 |
| 10 | 67 |
| 20 | 140 |
| 30 | 272 |
| 40 | 419 |
| 50 | 570 |
| 60 | 333 |

COMPARATIVE EXAMPLE WITH MANDELONITRILE

Operating conditions:

mandelonitrile 7 mM protein 5 μg/ml phosphate buffer 100 mM, pH 7.0 1 ml temperature 30° C.

| Time (minute) | Activity (μmol/h · mg of prot.) | ee |
|---|---|---|
| 15 | 1000 | i |
| 60 | 1030 | 1 |

The purified nitrilase is thus enantioselective on mandelonitrile but not on 4-methylthio-2-hydroxybutyronitrile.

EXAMPLE 7

Hydrolysis of 4-methylthio-2-hydroxybutyronitrile with Rhodococcus HT 29-7 FERM BP-3857

The microorganism *Rhodococcus sp.* HT 29-7 FERM BP-3857 is cultured in the following medium:

glycerol 20 g/l yeast extract (DIFCO) 3 g/l $KH_2PO_4$ 1 g/l

Na$_2$HPO$_4$.12H$_2$O 4.4 g/l
Na$_2$SO$_4$ 2.8 g/l
MgCl$_2$.6H$_2$O 0.85 g/l
CaCl$_2$.2H$_2$O 0.05 g/l
MnSO$_4$.H$_2$O 0.033 g/l
FeSO$_4$.7H$_2$O 0.013 g/l
ZnSO$_4$.7H$_2$O 0.005 g/l
benzonitrile 0.5 g/l
pH 7.5

The culturing is performed at 30° C. in 2 liter conical flasks containing 600 ml of medium. The whole mixture is stirred at 150 revolutions per minute for 140 hours. The cell pellet is recovered, washed with 9 g/l NaCl solution and then frozen.

Influence of the pH on the hydrolysis:
Operating conditions:
4-methylthio-2-hydroxybutyronitrile 100 mM
optical density at 660 nm 15
acetate buffer 100 mM of pH 4 to 5
phosphate buffer 100 mM of pH 6.0 to 7.0 1 ml
Tris-HCl buffer 100 mM of pH 8.0 to 9.0
borate buffer 100 mM of pH 10.0 to 11.0
temperature 30° C.
duration 10 hours

| pH | Yield of acid |
|---|---|
| 4 | 0% |
| 5 | 100% |
| 6 | 100% |
| 7 | 100% |
| 8 | 100% |
| 9 | 100% |
| 10 | 20% |
| 11 | 0% |

EXAMPLE 8

Influence of the Concentration of Substrate

The stability of the enzyme as a function of the amount of substrate was also measured under the following conditions:
4-methylthio-2-hydroxybutyronitrile cf Table of results
optical density at 660 nm 20
phosphate buffer 300 mM, pH 7.0 5 ml
temperature 30° C.
duration 2 hours

| Nitrile concentration (mM) | Yield of acid |
|---|---|
| 50 | 90% |
| 100 | 44% |
| 200 | 22% |
| 300 | 10% |
| 400 | 0% |
| 500 | 0% |

EXAMPLE 9

Stability of the Enzyme as a Function of the Amount of Acid Formed

Operating conditions:
4-methylthio-2-hydroxybutyronitrile 100 mM
optical density at 660 nm 15
phosphate buffer 100 mM, pH 7.0 1 ml
temperature 30° C.
duration 6 hours

| Acid concentration (mM) | Yield of acid |
|---|---|
| 0 | 100% |
| 200 | 100% |
| 400 | 100% |
| 600 | 100% |
| 800 | 100% |
| 1000 | 100% |

EXAMPLE 10

Enantiomeric excess
4-methylthio-2-hydroxybutyronitrile 140 mM
optical density at 660 nm 14
phosphate buffer 100 mM, pH 7.0 1 ml
temperature 20° C.

| Incubation time | Yield of acid | Optical purity |
|---|---|---|
| 2 h | 15% | 0 |
| 6 h | 50% | 0 |
| 24 h | 100% | 0 |

Study of the kinetics of hydrolysis of the 4-methylthio-2-hydroxybutyronitrile shows a linear production of hydroxy analogue of methionine per hour per mg of dry cells. The enantiomeric excess of the acid formed was measured by liquid chromatography; it is equal to 0% for a yield of acid ranging from 15% to 100%.

EXAMPLE 11

Influence of the Temperature

Operating Conditions:
4-methylthio-2-hydroxybutyronitrile 100 mM
optical density at 660 nm 15
phosphate buffer 100 mM, pH 7.0 1 ml
temperature see table
duration 6 hours

| T (°C.) | Yield of acid |
|---|---|
| 10 | 70% |
| 20 | 100% |
| 30 | 100% |
| 40 | 100% |
| 50 | 31% |
| 60 | 15% |

EXAMPLE 12

Hydrolysis of 4-methylthio-2-aminobutyronitrile

Operating Conditions:
4-methylthio-2-hydroxybutyronitrile 23 mM
optical density at 660 nm 15 phosphate buffer 100 mM, pH 7.0 1 ml
temperature 30° C.

| Time (hours) | Yield of acid | Enantiomeric excess of the acid |
|---|---|---|
| 0.5 | 40% | n.d. |
| 1 | 51% | 0.12 |
| 2 | 62% | n.d. |
| 5 | 78% | 0.15 |

EXAMPLE 13

Culture conditions used for *Gordona terrae* MA-1 (FERM BP-4535) are as follows:
glycerol 10 g/l
yeast extract 0.4 g/l
$K_2HPO_4$ 6.8 g/l
$Na_2HPO_4.12H_2O$ 7.1 g/l
$Na_2SO_4$ 2.8 g/l
$MgCl_2.6H_2O$ 0.4 g/l
$CaCl_2.2H_2O$ 40 mg/l
$MnSO_4.H_2O$ 4 mg/ml
$FeCl_3$ 0.6 mg/l
$ZnSO_4$ 0.3 mg/l
benzonitrile 0.5 g/l
pH 7.2
Activity of the enzyme The cultured cells are next washed and then placed in contact with the hydroxymethylthiobutyronitrile in order to assay the activity.
Operating conditions:
[nitrile]=23 mM;
[cells]=6.8 g/l;
phosphate buffer 100 mM
pH 7.0, 35° C.

The kinetics of hydrolysis of the hydroxymethylthiobutyronitrile are linear. The initial rate is estimated at 13 mmol/h.g dry cells.

EXAMPLE 14

Influence of the Concentration of Cyanohydrin of AMTP on the Nitrilase Activity

The influence of the initial concentration of hydroxymethylthiobutyronitrile on the nitrilase activity was determined, and the results are indicated in the following table.
Operating conditions:
[cells]=5.1 g/l;
phosphate buffer 100 mM
pH 7.0; 35° C.
The kinetics are effected over 0.5, 1, 2 and 3 hours.

| Nitrile concentration (mM) | Activity (mmol/h · g dry cells) |
|---|---|
| 50 | 14 |
| 100 | 13 |
| 200 | 15 |
| 300 | 0 |
| 400 | 0 |

Up to 200 mM, the activity varies little with the concentration of substrate.

EXAMPLE 15

Influence of the Concentration of Hydroxy Analogue of Methionine on the Nitrilase Activity In this test, we studied the influence of the concentration of ammonium 4-hydroxy-2-methylthiobutanoate on the nitrilase activity.
Operating conditions:

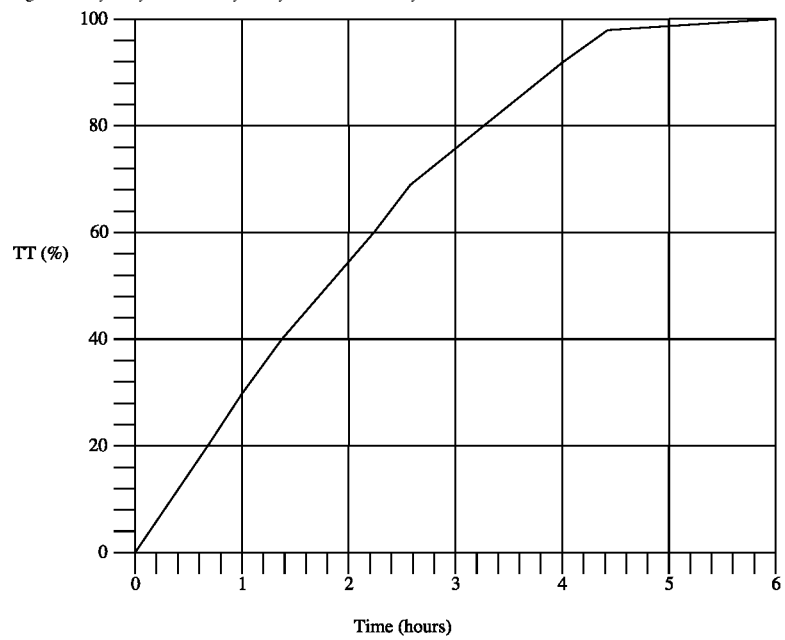

Figure 3: Hydrolysis of the cyanohydrin of AMTP by Gordona terrae MA-1.

[cells]=5 g/l;
[nitrile]=100 mM;
phosphate buffer 100 mM, pH 7.0; 35° C.

The concentration of ammonium carboxylate varies between 0 and 1.5M.

| Acid concentration (mol/l) | Activity (μmol/h · mg of dry cells) |
|---|---|
| 0 | 9.4 |
| 0.5 | 14 |
| 1 | 19 |
| 1.5 | 15 |

The concentration of ammonium 4-hydroxy-2-methylthiobutanoate does not at all modify the initial activity of the strain Gordona terrae HT29-7.

EXAMPLE 16

Influence of the pH and of the Temperature

Operating conditions:
[nitrile]=100 mM;
[cells]=7.5 g/l;
acetate buffer 100 mM, pH 4 to 5;
phosphate buffer 100 mM, pH 6 to 7;
Tris-HCl buffer 100 mM, pH 8 to 9
borate buffer 100 mM, pH 10 to 11; 3
30° C.; kinetics over 1, 2, 4 and 6 hours.

| pH | Activity (mmol/h   g dry cells) |
|---|---|
| 4 | 0.6 |
| 5 | 2.5 |
| 6 | 7.8 |
| 7 | 9.6 |
| 8 | 15.3 |
| 9 | 18 |
| 10 | 5.7 |
| 11 | 11 |

The optimum pH is at about 8–9 under our operating conditions.

Influence of the temperature on the nitrilase activity of *Gordona terrae* MA-1.

Operating conditions:
[nitrile]=100 mM;
[cells]=7.5 g/l;
phosphate buffer 100 mM, pH 7.0;
kinetics over 1 hour.

| T (°C.) | Activity (mmol/h · g dry cells) |
|---|---|
| 10 | 0.6 |
| 20 | 2.3 |
| 30 | 3.2 |
| 40 | 3.4 |
| 50 | 3.5 |
| 60 | 1.9 |

The optimum temperature is about 40°–50° C.

We claim:

1. A process for preparing a racemic α-substituted 4-methylthiobutyric acid, comprising:

(a) hydrolyzing a racemic α-substituted 4-methylthiobutyronitrile with a nitrilase from a microorganism selected from the group consisting of *Alcaligenes faecalis* (ATCC 8750), *Rhodococcus sp.* HT 29-7 (FERM BP-3857), and *Gordona terrae* MA-1 (FERM BP-4535); and (b) recovering the racemic α-substituted 4-methylthiobutyric acid.

2. The process according to claim 1, wherein the racemic α-substituted 4-methylthiobutyronitrile is 4-methylthio-2-hydroxybutyronitrile.

3. The process according to claim 1, wherein the pH of the process is between 4 and 11.

4. The process according to claim 3, wherein the pH is between about 5 and about 9.

5. The process according to claim 1, wherein the hydrolysis temperature is between 30° and 60° C.

6. The process according to claim 5, wherein the temperature is between about 30° C. and about 50° C.

7. The process according to claim 1, wherein the concentration of the α-substituted 4-methylthiobutyronitrile is between 10 and 400 mmol per liter of starting solution.

8. The process according to claim 7, wherein the concentration of the α-substituted 4-methylthiobutyronitrile is between about 50 and about 200 mmol per liter.

9. The process according to claim 1, wherein the concentration of the α-substituted 4-methylthiobutyric acid formed is between 10 and 2000 mmol per liter.

10. The process according to claim 9, wherein the concentration of the α-substituted 4-methylthiobutyric acid is between about 100 and about 1500 mmol per liter.

11. The process according to claim 1, wherein the nitrilase is from the microorganism *Alcaligenes faecalis* (ATCC 8750).

12. The process according to claim 1, wherein the nitrilase is from the microorganism *Rhodococcus sp.* HT 29-7 (FERM BP-3857).

13. The process according to claim 1, wherein the nitrilase is from the microorganism *Gordona terrae* MA-1 (FERM BP-4535).

14. The process according to claim 1, wherein the nitrilase is a free or immobilized enzyme of the microorganism.

15. The process according to claim 14, wherein the enzyme is partially or totally purified.

* * * * *